(12) United States Patent (10) Patent No.: US 7,734,354 B1
Cox (45) Date of Patent: Jun. 8, 2010

(54) STIMULATION LEAD, STIMULATION SYSTEM, AND METHOD FOR LIMITING MRI INDUCED CURRENT IN A STIMULATION LEAD

(75) Inventor: Timothy J Cox, Leonard, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 481 days.

(21) Appl. No.: 11/833,801

(22) Filed: Aug. 3, 2007

Related U.S. Application Data

(60) Provisional application No. 60/821,419, filed on Aug. 4, 2006.

(51) Int. Cl.
*A61N 1/16* (2006.01)
(52) U.S. Cl. ...................................... 607/116
(58) Field of Classification Search .................. 607/116
See application file for complete search history.

(56) References Cited

U.S. PATENT DOCUMENTS

| | | | |
|---|---|---|---|
| 6,985,775 | B2 | 1/2006 | Reinke et al. |
| 7,174,219 | B2 | 2/2007 | Wahlstrand et al. |
| 7,363,090 | B2 | 4/2008 | Halperin et al. |
| 2003/0144720 | A1 | 7/2003 | Villaseca et al. |
| 2005/0222656 | A1 | 10/2005 | Wahlstrand et al. |
| 2005/0222657 | A1 | 10/2005 | Wahlstrand et al. |
| 2005/0222658 | A1 | 10/2005 | Hoegh et al. |
| 2005/0222659 | A1 | 10/2005 | Olsen et al. |
| 2006/0229693 | A1 | 10/2006 | Bauer et al. |
| 2006/0247747 | A1 | 11/2006 | Olsen et al. |
| 2006/0247748 | A1 | 11/2006 | Wahlstrand et al. |
| 2007/0088416 | A1 | 4/2007 | Atalar et al. |
| 2007/0112398 | A1 | 5/2007 | Stevenson et al. |
| 2007/0185556 | A1 | 8/2007 | Williams et al. |
| 2007/0208383 | A1 | 9/2007 | Williams |
| 2007/0299490 | A1 | 12/2007 | Yang et al. |
| 2008/0009905 | A1 | 1/2008 | Zeijlemaker |
| 2008/0033497 | A1 | 2/2008 | Bulkes et al. |
| 2008/0116997 | A1 | 5/2008 | Dabney et al. |
| 2008/0119919 | A1 | 5/2008 | Atalar et al. |
| 2008/0203966 | A1 | 8/2008 | Ward |
| 2008/0243218 | A1 | 10/2008 | Bottomley et al. |
| 2008/0262584 | A1 | 10/2008 | Bottomley et al. |

*Primary Examiner*—Carl H Layno
*Assistant Examiner*—Yun Haeng Lee
(74) *Attorney, Agent, or Firm*—Christopher S. L. Crawford; Peter Lando; Melissa Acosta

(57) ABSTRACT

In one embodiment, an implantable lead for electrical stimulation of a patient, comprises: a bidirection frequency dependent current limiter (BFDCL) circuit that limits a magnitude of current that can flow through the at least one conductor from the at least one terminal to the at least one electrode, wherein the BFDCL circuit comprises: a passive frequency dependent network element; first and second semiconductors that each comprise source, drain, and reference terminals, wherein the source terminals of the first and second semiconductors are coupled to respective ends of the passive frequency dependent network element, the source terminal of the first semiconductor is coupled to the gate terminal of the second semiconductor, and the source terminal of the second semiconductor is coupled to the gate terminal of the first semiconductor.

18 Claims, 3 Drawing Sheets

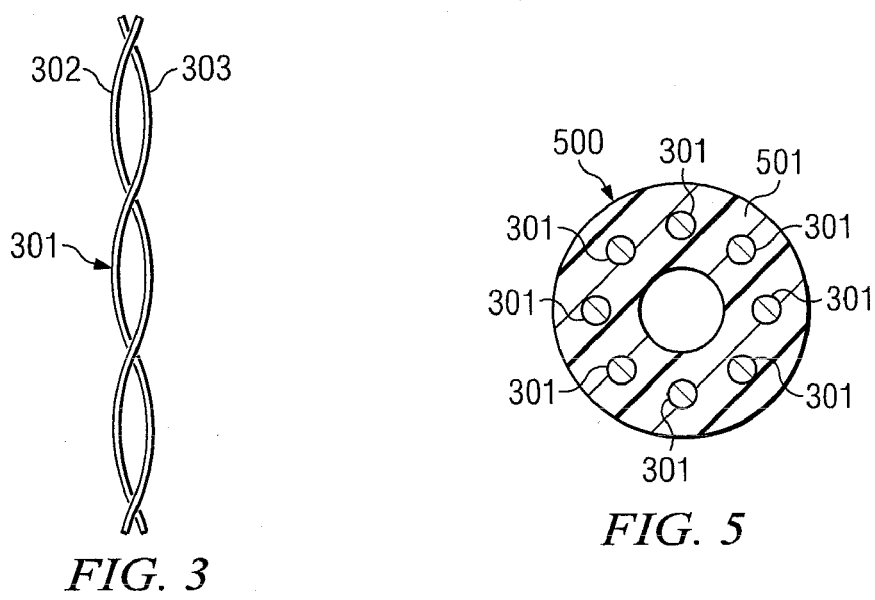
FIG. 3
FIG. 5
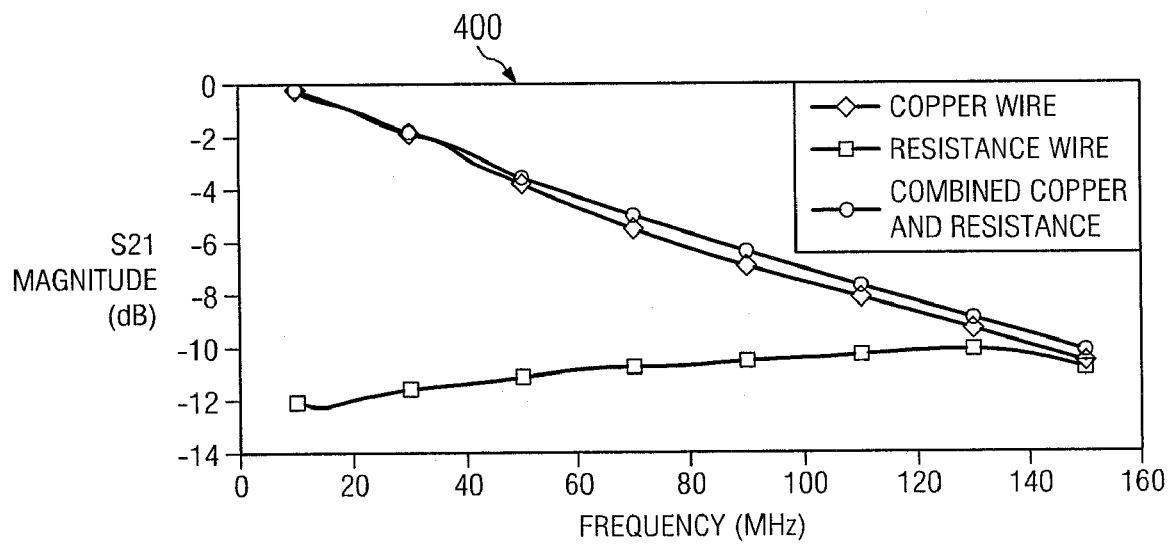
FIG. 4

STIMULATION LEAD, STIMULATION SYSTEM, AND METHOD FOR LIMITING MRI INDUCED CURRENT IN A STIMULATION LEAD

CROSS-REFERENCE TO RELATED APPLICATIONS

This application claims the benefit of U.S. Provisional Application No. 60/821,419, filed Aug. 4, 2006, the disclosure of which is incorporated herein by reference.

TECHNICAL FIELD

The present application is generally related to limiting MRI induced current in a stimulation lead such as a neurostimulation lead, a cardiac stimulation lead, and/or the like.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or several leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

There are concerns related to the compatibility of neurostimulation systems with magnetic resonance imaging (MRI). MRI generates cross-sectional images of the human body by using nuclear magnetic resonance (NMR). The MRI process begins with positioning the patient in a strong, uniform magnetic field. The uniform magnetic field polarizes the nuclear magnetic moments of atomic nuclei by forcing their spins into one of two possible orientations. Then an appropriately polarized pulsed RF field, applied at a resonant frequency, forces spin transitions between the two orientations. Energy is imparted into the nuclei during the spin transitions. The imparted energy is radiated from the nuclei as the nuclei "relax" to their previous magnetic state. The radiated energy is received by a receiving coil and processed to determine the characteristics of the tissue from which the radiated energy originated to generate the intra-body images.

Neurostimulation systems are designated as being contraindicated for MRI, because the time-varying magnetic RF field causes the induction of current which, in turn, can cause significant heating of patient tissue due to the presence of metal in various system components. The induced current can be "eddy current" and/or current caused by the "antenna effect."

"Eddy current" refers to current caused by the change in magnetic flux due to the time-varying RF magnetic field across an area bounding conductive material (i.e., patient tissue). As shown in a simplified form in FIG. 1, the time-varying magnetic RF field induces current within the tissue of a patient that flows in closed-paths. When conventional pulse generator 103 and conventional implantable lead 104 are placed within tissue in which eddy currents are present, implantable lead 104 and pulse generator 103 provide a low impedance path for the flow of current. As depicted in FIG. 1, electrode 102 provides a conductive surface that is adjacent to current path 101. Electrode 102 is coupled to pulse generator 103 through a wire conductor (not shown) within implantable lead 104. The metallic housing (the "can") of pulse generator 103 also provides a conductive surface in the tissue in which eddy currents are present. Thus, current can flow from the tissue through electrode 102 and out the metallic housing of pulse generator 103. Because of the low impedance path and the relatively small surface area of electrode 102, the current density in the patient tissue adjacent to electrode 102 can be relatively high. Accordingly, resistive heating of the tissue adjacent to electrode 102 can be high and can cause significant tissue damage.

Also, the "antenna effect" can cause current to be induced which can result in undesired heating of tissue. Specifically, depending upon the length of the stimulation lead and its orientation relative to the time-varying magnetic RF field, the wire conductors of the stimulation lead can each function as an antenna and a resonant standing wave can be developed in each wire. A relatively large potential difference can result from the standing wave thereby causing relatively high current density and, hence, heating of tissue adjacent to the electrodes of the stimulation lead.

BRIEF DESCRIPTION OF THE DRAWINGS

FIG. 3 depicts a conductive wire pair adapted for an MRI compatible lead according to one representative embodiment.

FIG. 4 depicts a transmission factor chart for a conductive wire pair according to one representative embodiment.

FIG. 5 depicts a stimulation lead according to one representative embodiment.

SUMMARY

Figure 6:
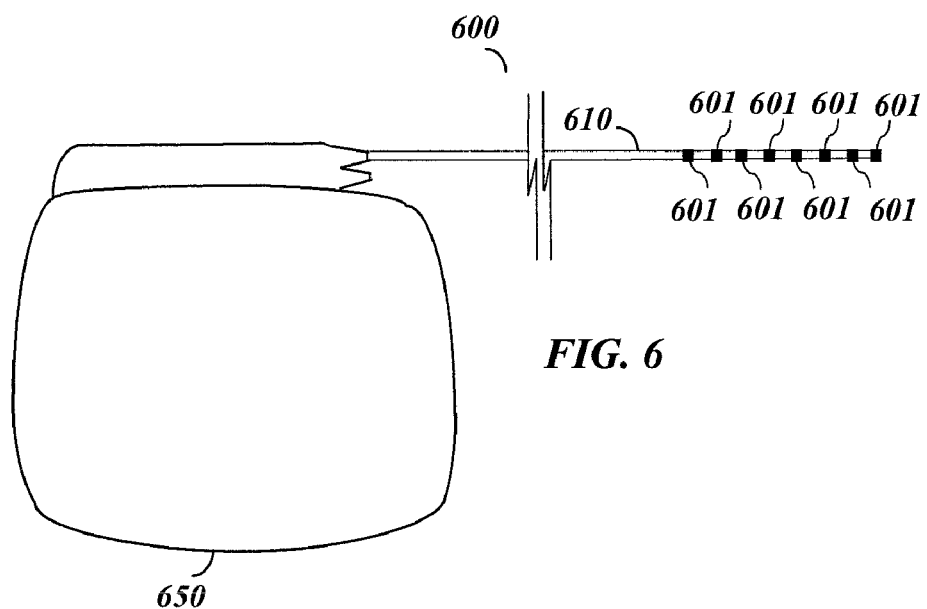
FIG. 6 depicts a stimulation system according to one representative embodiment.
Figure 1:
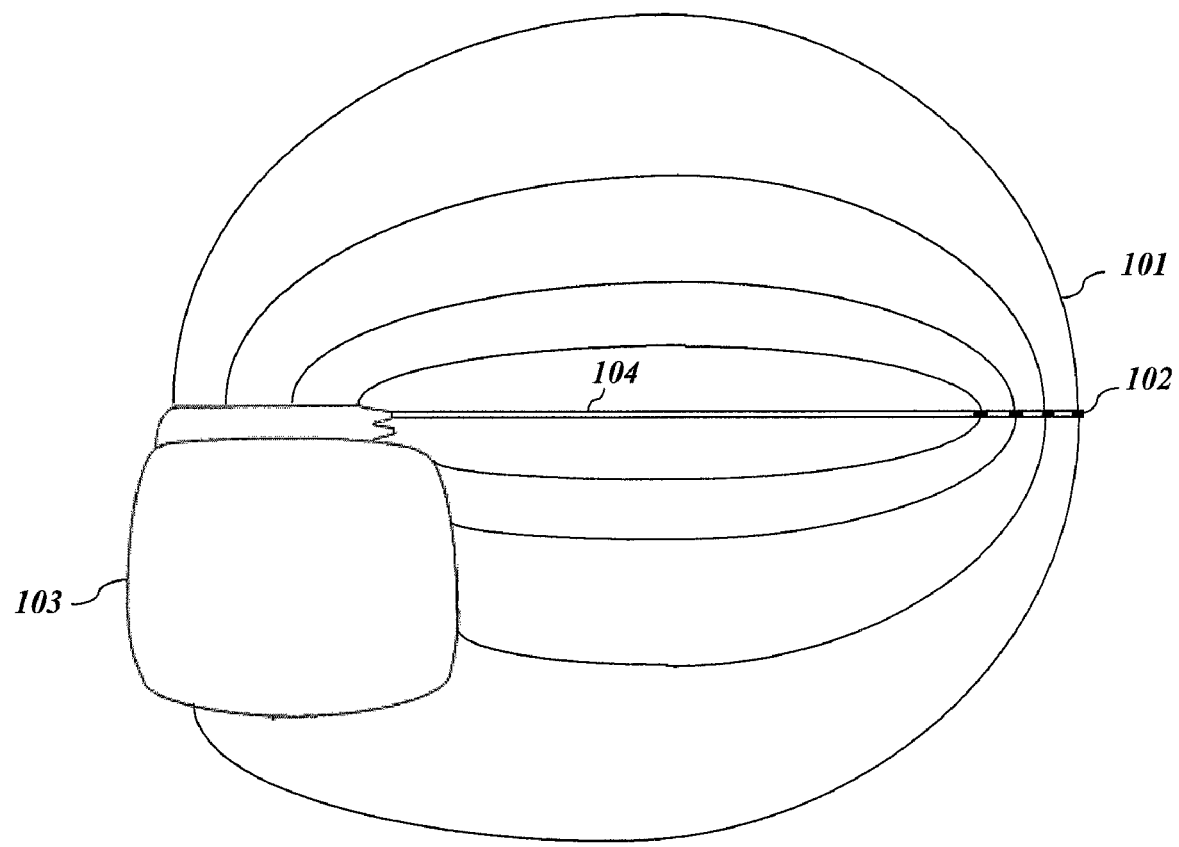
FIG. 1 depicts a pulse generator and implantable lead subjected to eddy current induced by the time-varying RF field of a MRI scan.

In one embodiment, an implantable lead for electrical stimulation of a patient, comprises: a bidirection frequency dependent current limiter (BFDCL) circuit that limits a magnitude of current that can flow through the at least one conductor from the at least one terminal to the at least one electrode, wherein the BFDCL circuit comprises: a passive frequency dependent network element; first and second semiconductors that each comprise source, drain, and reference terminals, wherein the source terminals of the first and second semiconductors are coupled to respective ends of the passive frequency dependent network element, the source terminal of the first semiconductor is coupled to the gate terminal of the second semiconductor, and the source terminal of the second semiconductor is coupled to the gate terminal of the first semiconductor.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Some representative embodiments are directed to a MRI compatible lead for stimulation of a patient. The lead can be adapted in a number of ways to reduce the amount of current that can flow through the lead due to MRI induced currents. In some representative embodiments, a bidirectional frequency dependent current-limiter (BFDCL) circuit is provided in the lead (e.g., adjacent to each electrode or terminal) to limit the amount of current that can flow through each conductive wire of the stimulation lead. The BFDCL circuit allows low frequency components of current to pass through the circuit with negligible potential drop. However, the sinusoidal potential drop (across the BFDCL circuit) caused by MRI-induced current flow may become large enough to impede current flow that exceeds a safe current level.

In additional embodiments, the stimulation lead further contains wire conductors that exhibit relatively low impedance at frequencies used for stimulation of a patient and relatively high impedance at frequencies used by MRI systems during RF pulse sequences. The frequency dependent impedance of the wire conductors further limit the MRI-induced current in the stimulation leads. By limiting the MRI-induced current, resistive heating of patient tissue is avoided or substantially mitigated.

Figure 2A:
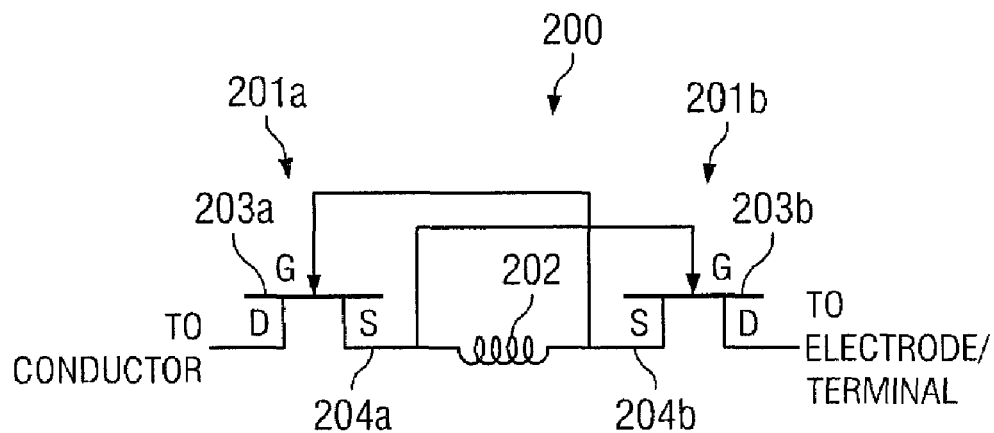
FIG. 2A depicts a bidirectional frequency dependent limiter that can be used in a stimulation lead according to one representative embodiment.

FIG. 2A depicts bidirectional frequency dependent limiter circuit 200 that can be used in a stimulation lead according to one representative embodiment. Circuit 200 comprises three terminal semiconductors 201a and 201b in series with a two terminal frequency-dependent passive network 202 (e.g., an inductor). Semiconductors 201a and 201b are adapted so that their channel resistance increases as the gate voltage is increased. Examples of suitable semiconductors include a depletion-mode MOSFET and a junction Field Effect Transistor. In preferred embodiments, the semiconductors are implemented on flexible substrates as will be discussed herein below.

As shown in FIG. 2A, each of semiconductors 201a and 201b has a reference terminal (the "gate") coupled to the source terminal of the other semiconductor. The reference terminals are depicted by 203a and 203b and the source terminals are depicted by 204a and 204b. The drain terminals of semiconductors 201a and 201b are electrically coupled to a wire conductor of the lead and an electrode or terminal of the lead.

As current flows through circuit 200, a voltage drop occurs across inductor 202 in the direction of the current flow. As previously discussed, the source terminals 204a and 204b of semiconductors 201a and 201b are respectively coupled to respective ends of inductor 202. Also, the reference or gate terminal 203a and 203b are coupled to the opposite ends of inductor 202. Thus, the voltage between the gate 203 and the source 204 of one of semiconductors 201 is always negative when an AC current flows through circuit 200. The negative gate to source voltage increases the resistance of the channel of the semiconductor 201. For example, suppose the node coupled to source 204a is at a higher voltage than the node coupled to source 204b, a negative gate to source voltage would be applied to semiconductor 201b and the channel resistance of semiconductor 201b would be increased.

For low frequency components of stimulation currents (current provided by a pulse generator for conventional stimulation applications), the potential drop applied to the respective semiconductor 201 is negligible and does not appreciably affect stimulation pulses from the pulse generator. However, at the radio frequency of an MRI system (e.g., 64 MHz), the sinusoidal potential drop caused by the MRI-induced current flow may become sufficiently large to cause the semiconductors 201 (alternatively in successive half cycles) to impede current flow from increasing beyond a maximum magnitude. The maximum current magnitude permitted by circuit 200 is controlled by the frequency-dependent passive network (e.g., inductor 202) and the activation threshold of semiconductors 201.

Circuit 200 provides several beneficial characteristics for integration into a stimulation lead. For example, circuit 200 does not require external power and, hence, a DC power line is not required at the electrodes of a stimulation lead to limit MRI induced current. Circuit 200 can be readily miniaturized using integrated circuit technologies and, in one preferred embodiment, circuit 200 is implemented on a flexible substrate that is disposed underneath a respective electrode. Additionally, any excessive high frequency current that may cause thermal damage to tissue is impeded (not just MRI induced currents). Circuit 200 can be inherently tolerant of 1.5 T, 3 T, and higher Telsa MRI systems. Also, circuit 200 is not solely dependent upon the inductor to limit current and, therefore, an excessive number of inductor windings is not necessary.

Figure 2B:
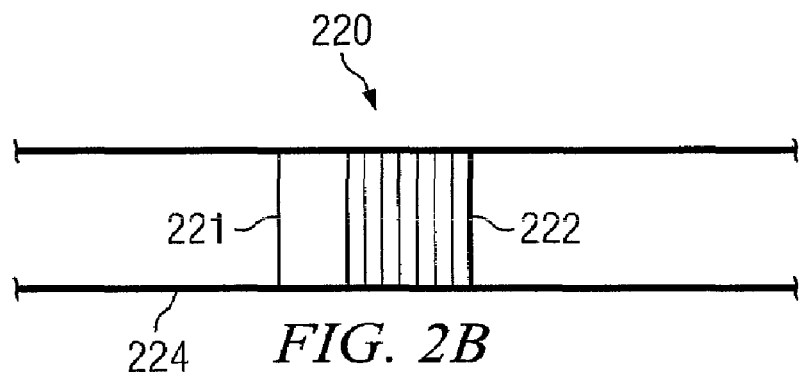
FIG. 2B depicts a portion of a stimulation lead according to one representative embodiment.

FIG. 2B depicts a portion of stimulation lead 220 according to one representative embodiment. Stimulation lead 220 comprises lead body 224 of an insulative material in which multiple conductive wires (not shown) are embedded. At a suitable point at the distal end of stimulation lead 220, flex circuit 221 is applied to stimulation lead 220.

Figure 2C:
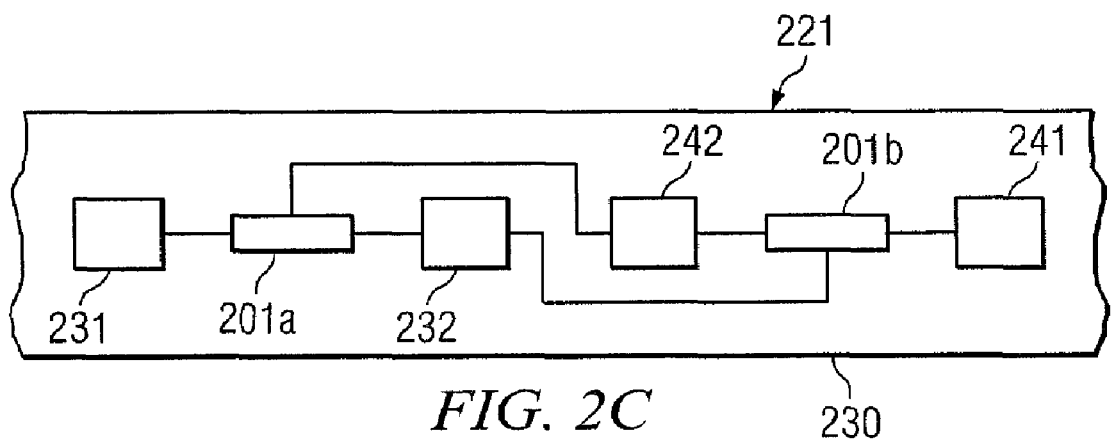
FIG. 2C depict a flex circuit that includes semiconductors and contact pads for a bidirectional frequency dependent limiter according to one representative embodiment.

Referring to FIG. 2C, flex circuit 221 comprises flexible substrate 230 on which semiconductors 201a and 201b are formed. Flexible circuit 221 further comprises contact pads 231 and 232 that are electrically coupled to the drain and source terminals of semiconductor 201a. Flexible circuit 221 further comprises contact pads 241 and 242 that are electrically coupled to the drain and source terminals of semiconductor 201b. Contact pads 231, 232, 241, and 242 are provided to facilitate further electrical connections during lead assembly operations. Also, contact pads 232 and 242 are preferably coupled to the terminals of the other semiconductors 201a and 201b using conductive lines deposited on the flexible substrate 230.

The flexible substrate enables flex circuit 221 to be readily applied to the outer surface of lead body 224 as shown in FIG. 2B. Flex circuit 221 can placed around lead body 224 such that the back of flexible substrate 230 is exposed and semiconductors 201a and 201b and contact pads 231, 232, 241, and 242 are adjacent to the insulative material of lead body 224. In alternative embodiments, separate flexible substrates could be utilized for semiconductors 201a and 201b and their contact pads.

During lead fabrication, an aperture (not shown) is preferably created in lead body 224 to provide access to one of the conductive wires of the stimulation lead. An electrical connection (not shown) is made to the exposed conductive wire of the lead body (e.g., by building up conductive material within the aperture, applying conductive epoxy, using a bridging wire, etc.) to contact pad 231 of flex circuit 221. Specifically, this connection is used to electrically connect the drain terminal of semiconductor 201a via conductive pad 231 to the conductive wire of the lead body.

Contact pads 232 and 242 of flex circuit 221 are then coupled to the two terminals of inductor 222 using, for example, respective bridging wires (not shown). In some representative embodiments, one or several layers of an insulated wire conductor are wound about lead body 224 to implement the inductor. The wire conductor may be initially wound about a bobbin structure or other cylindrical package and laterally placed over the lead body 224 during lead fabrication. Alternatively, the wire conductor may be directly wound around lead body 224 using a suitable winding device.

In one embodiment, a bridging wire (not shown) may be connected to contact pad 242 to facilitate an electrical contact with an electrode which is preferably placed or fabricated over the top of flex circuit 221 and inductor 222. In another embodiment, conductive material is deposited on the backside of flexible substrate 230 and conductive pad 242 is electrically connected to the conductive material (e.g., through a "via" in the flexible substrate 230) to facilitate electrical contact with the electrode.

Referring now the conductive wires of the stimulation lead, FIG. 3 depicts conductive wire pair 301 adapted for an MRI compatible lead according to one representative embodiment. Conductive wire pair 301 comprises a low electrical conductivity wire 302 and a high electrical conductivity wire 303. Conductive wire pair 301 can be used as a coupling conductor between a connector or terminal at a proximal end of a lead body to one or several electrodes at a distal end of the lead body or on a paddle structure.

High electrical conductivity wire 303 possesses a low resistance at frequencies used for stimulation of the patient (e.g., generally under 1000 Hz) due to the material characteristics of wire 303. However, the resistance of the high electrical conductivity wire 303 is significantly increased at high frequencies due to the skin effect. The skin effect refers to the tendency of an alternating electric current to distribute itself within a conductor so that the current density near the surface of the conductor is greater than that at its core. That is, the electric current tends to flow at the "skin" of the conductor. In some embodiments, the outside diameter (OD) of the high electrical conductivity wire 303 is relatively small (e.g. approximately 1.0 thousandth of an inch) to contribute to the degree that the skin effect increases the resistance at MRI frequencies. High conductivity wire 303 is preferably wound around or twisted with low conductivity wire 302 to provide strength and durability. Low conductivity wire 302 preferably possesses an outside diameter of similar size to the outside diameter of wire 303. In comparison to wire 303, the resistance of wire 302 varies by a relatively small amount from low to high frequencies.

Wires 302 and 303 are preferably disposed in a twisted or helically wound arrangement. The wound arrangement shown in FIG. 3 depicts an amount of separation between wires 302 and 303 for the sake of clarity in the illustration. However, relatively little (if any) interstitial space between wires 302 and 303 is present after the winding together of wires 302 and 303 according to preferred embodiments. Low conductivity wire 302 provides a degree of strength and durability to wire 303 when wires 302 and 303 are wound together. When wires 302 and 303 are wound together, current from low frequency stimulation pulses generally flows in wire 303 due to the relatively low resistance of the wire 303 at lower frequencies. Current at higher frequencies, such as those induced by MRI induction, flows mainly in wire 302. This occurs, because the skin effect in wire 303 causes the impedance of wire 303 to become larger than the impedance of wire 302 which does not exhibit a skin effect. Additionally, when wound together, wire 303 tends to function as an inter-turn shield at very high frequencies.

As an example, by implementing wire 302 using nichrome with 0.83 thousandth of an inch OD and wire 303 using copper with 1.0 thousandth of an inch OD, the DC resistance of wire pair 301 would be approximately 100 Ohms per foot while the resistance at 64 MHz would be 4500 Ohms per foot. Accordingly, wire pair 301 is well suited for neurostimulation applications, because wire pair 301 significantly reduces the current present at MRI frequencies without requiring an undue amount of power from a pulse generator at stimulation frequencies. In some embodiments, wire 302 could be alternatively implemented using a non-conductive or other polymer core with a thin magnetic coating which would allow a higher level of attenuation at MRI frequencies.

FIG. 4 depicts transmission factor chart 400 for a wire conductor pair according to one representative embodiment. In chart 400, the horizontal axis represents the frequency of signal applied using a vector network analyzer (VNA). The horizontal axis reflects the frequency of the stimulus signal (as applied to the proximal end of the wire conductor pair at "port 1" of the VNA) and the vertical axis reflects the S21 measurement. The S21 measurement is the ratio of the amplitude of the response signal (the signal at the distal end of the wire conductor pair measured at "port 2" of the VNA) to the amplitude of the stimulus signal. As seen in chart 400, the signal transmission of the wire conductor pair substantially follows the transmission of the copper wire that is, in turn, defined by the skin effect. As reflected in chart 400, the impedance of the wire pair is relatively low at low frequencies and is much higher at MRI frequencies.

FIG. 5 depicts a cross-sectional view of stimulation lead 500 according to one representative embodiment. Stimulation lead 500 comprises a plurality of wire conductor pairs 301 that exhibit a frequency-dependent impedance such that relatively low amounts of current are induced into conductor pairs 301 during MRI. Pairs 301 are maintained in electrical isolation from each other by the insulative polymer or silicone material forming lead body 501. It shall be appreciated that any suitable number of pairs 301 could be included within lead 500. Also, in alternative embodiments, multiple layers of pairs 301 could be employed.

FIG. 6 depicts stimulation system 600 according to one representative embodiment. Stimulation system 600 includes pulse generator 650 coupled to one or several leads 610. Pulse generator 650 can be implemented using a commercially available pulse generator such as the Eon™ rechargeable IPG available from Advanced Neuromodulation Systems (Plano, Tex.). Any other currently available or subsequently developed pulse generator could also be used. Pulse generator 650 generates electrical pulses for neurostimulation of the patient. Pulse generator 650 is electrically coupled to lead 610 using a header structure that connects the pulse generator circuitry within the housing of pulse generator to terminals (not shown) of lead 610. Each terminal or connector is, in turn, electrically connected to a respective conductive wire within the interior of the lead to conduct the electrical pulses through lead 500 to a corresponding electrode 601. Although lead 610 is depicted as a percutaneous lead in FIG. 4, lead 610 could alternatively possess a paddle structure for electrodes 601.

Stimulation system 600 is adapted to mitigate or reduce MRI induced currents by utilizing BFDCL circuit 200 and/or by utilizing conductor pairs 301 in lead 610. In some embodiments, BFDCL circuits 200 are disposed between electrodes 601 and the wire conductors of lead 610. Alternatively, BFDCL circuits 200 can be disposed between the terminals of lead 610 and the wire conductors of lead 610.

Although stimulation of the spinal cord has been discussed, some embodiments can be utilized to deliver stimulation pulses for other therapeutic purposes such as deep brain stimulation, cortical stimulation, peripheral nerve stimulation, cardiac pacemakers, defibrillation devices, gastric pacing, etc. Additionally, lead extensions can be adapted to include BFDCL circuits 200 and/or frequency dependent wire conductors according to some representative embodiments. Some embodiments could be utilized solely for diagnostic purposes. For example, a medical cable can be extended from a patient in an MRI bore to exterior monitoring equipment to allow physiological signals (such as EKG signals) to be monitored during an MRI exam. The medical cable can be implemented to include BFDCL circuits 200 and/or frequency dependent wire conductors.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. An implantable lead for electrical stimulation of a patient, comprising:
   at least one terminal for receiving electrical stimulation;
   at least one electrode for delivering electrical stimulation to tissue of the patient;
   a lead body of an insulative material;
   at least one conductor within the insulative material that electrically couples the at least one terminal with the at least one electrode; and
   a bidirection frequency dependent current limiter (BFDCL) circuit that limits a magnitude of current that can flow through the at least one conductor from the at least one terminal to the at least one electrode, wherein the BFDCL circuit comprises:
   a passive frequency dependent network element;
   first and second semiconductors that each comprise source, drain, and reference terminals, wherein the source terminals of the first and second semiconductors are coupled to respective ends of the passive frequency dependent network element, the source terminal of the first semiconductor is coupled to the reference terminal of the second semiconductor, and the source terminal of the second semiconductor is coupled to the reference terminal of the first semiconductor.

2. The stimulation lead of claim 1 wherein the passive frequency dependent network is selected from the list consisting of an inductor and a parallel inductor and capacitor network.

3. The stimulation lead of claim 2 wherein the inductor is implemented by looping a conductive wire around a lead body of the stimulation lead.

4. The stimulation lead of claim 1 wherein the first and second semiconductors are depletion mode MOSFETs.

5. The stimulation lead of claim 1 wherein the first and second semiconductors are junction FETs.

6. The stimulation lead of claim 1 wherein the first and second semiconductors are implemented on one or several flexible substrates.

7. The stimulation lead of claim 6 wherein the one or several flexible substrates are placed as one or several bands around a lead body of the stimulation lead.

8. The stimulation lead of claim 6 wherein each of the one or several flexible substrates comprises contact pads that are respectively electrically coupled to the drain terminal of a respective semiconductor.

9. An implantable stimulation system for electrically stimulating a patient, comprising:
   a pulse generator for generating electrical pulses; and
   a stimulation lead that comprises: at least one terminal for receiving electrical stimulation; at least one electrode for delivering electrical stimulation to tissue of the patient; a lead body of an insulative material; at least one conductor within the insulative material that electrically couples the at least one terminal with the at least one electrode; and a bidirection frequency dependent current limiter (BFDCL) circuit that limits a magnitude of current that can flow through the at least one conductor from the at least one terminal to the at least one electrode, wherein the BFDCL circuit comprises:
   a passive frequency dependent network element;
   first and second semiconductors that each comprise source, drain, and reference terminals, wherein the source terminals of the first and second semiconductors are coupled to respective ends of the passive frequency dependent network element, the source terminal of the first semiconductor is coupled to the reference terminal of the second semiconductor, and the source terminal of the second semiconductor is coupled to the reference terminal of the first semiconductor.

10. The stimulation system of claim 9 wherein the passive frequency dependent network is an inductor.

11. The stimulation system of claim 9 wherein the passive frequency dependent network is an inductor shunted by a capacitor.

12. The stimulation system of claim 9 wherein the first and second semiconductors are depletion mode MOSFETs.

13. The stimulation system of claim 9 wherein the first and second semiconductors are junction FETs.

14. The stimulation system of claim 1 wherein the first and second semiconductors are implemented on one or several flexible substrates.

15. The stimulation system of claim 14 wherein the one or several flexible substrates are placed as one or several bands around a lead body of the stimulation lead.

16. The stimulation system of claim 14 wherein each of the one or several flexible substrates comprises contact pads that are respectively electrically coupled to the drain terminal of a respective semiconductor.

17. The stimulation system of claim 14 wherein the pulse generator is a neurostimulator.

18. The stimulation system of claim 14 wherein the pulse generator is a cardiac rhythm management device.

* * * * *